United States Patent
Dannhardt et al.

(10) Patent No.: US 8,008,320 B2
(45) Date of Patent: Aug. 30, 2011

(54) 3-(INDOLYL)-4-ARYLMALEIMIDE DERIVATIVES AND THEIR USE AS ANGIOGENESIS INHIBITORS

(75) Inventors: Gerd Dannhardt, Mainz (DE); Christian Peifer, Türbingen (DE); Stanislav Plutizki, Mainz (DE); Jan-Peter Kramb, Türbingen (DE)

(73) Assignee: Johannes Gutenberg-Universitatis (DE)

( * ) Notice: Subject to any disclaimer, the term of this patent is extended or adjusted under 35 U.S.C. 154(b) by 448 days.

(21) Appl. No.: 11/721,292

(22) PCT Filed: Dec. 7, 2005

(86) PCT No.: PCT/EP2005/013126
§ 371 (c)(1),
(2), (4) Date: Jun. 24, 2009

(87) PCT Pub. No.: WO2006/061212
PCT Pub. Date: Jun. 15, 2006

(65) Prior Publication Data
US 2009/0306124 A1 Dec. 10, 2009

(30) Foreign Application Priority Data
Dec. 8, 2004 (EP) .................................. 04029069

(51) Int. Cl.
*A61K 31/4375* (2006.01)
*A61K 31/404* (2006.01)
*C07D 403/10* (2006.01)
*C07D 471/04* (2006.01)
(52) U.S. Cl. ......... 514/300; 514/414; 546/113; 548/465
(58) Field of Classification Search .................. 514/300, 514/414; 546/113; 548/465
See application file for complete search history.

(56) References Cited

U.S. PATENT DOCUMENTS

| 5,057,614 | A | 10/1991 | Davis et al. |
| 7,001,906 | B2 * | 2/2006 | Prudhomme et al. ......... 514/250 |
| 2004/0054180 | A1 | 3/2004 | Zhang et al. |
| 2004/0192718 | A1 | 9/2004 | Zhang et al. |

FOREIGN PATENT DOCUMENTS

| CA | 2010636 | 8/1990 |
| EP | 0540956 | 5/1993 |
| EP | 1224932 | 7/2002 |
| WO | WO 91/13071 | 9/1991 |
| WO | WO 95/07910 | 3/1995 |
| WO | WO 97/34890 | 9/1997 |
| WO | WO 00/21927 | 4/2000 |
| WO | WO 00/38675 | 7/2000 |
| WO | WO 02/10158 | 2/2002 |
| WO | WO 02/38561 | 5/2002 |
| WO | 03002563 | * 1/2003 |
| WO | WO 03/057202 | 7/2003 |
| WO | WO 03/095452 | 11/2003 |
| WO | WO 03/103663 | 12/2003 |
| WO | WO 2006/061212 | 6/2006 |

OTHER PUBLICATIONS

International Search Report for International Application No. PCT/EP2005/013126 (2006).
International Preliminary Report on Patentability for International Application No. PCT/EP2005/013126 (2006).
Zhang et al., "3-(7-Azaindolyl)-4-arylmaleimides as potent, selective inhibitors of glycogen synthase Kinase-3", *Bioorganic & Medicinal Chemistry Letters*, 14(12), 3245-3250 (2004).
Bokhari et al., "Regulation of Skin Microvasculature Angiogenesis, Cell Migration, and Permeability by a Specific Inhibitor of PKCα", *J. Invest. Dermatol.*, 2006, 126 (2), 460-467.
Cabebe et al., "Sunitinib: A newly approved small-molecule inhibitor of angiogenesis", *Drugs of Today*, 2006, 42 (6), 387-398.
Davis et al., "Inhibitors of protein kinase C. 1. 2,3-Bisarylmaleimides", *J. Med. Chem.*, 1992, 35, 177-184.
Davis et al., "Inhibitors of protein kinase C. 2. Substituted bisindolylmaleimides with improved potency and selectivity", *J. Med. Chem.*, 1992, 35, 994-1001.
Faul et al., "Cyclization strategies for the synthesis of macrocyclic bisindolylmaleimides", *J. Org. Chem.*, 2001, 66, 2024-2033.
Faul et al., "Acyclic N-(azacycloalkyl)bisindolylmaleimides: Isozyme selective inhibitors of PKCβ", *Bioorg. Med. Chem. Lett.*, 2003, 13, 1857-1859.
Faul et al., "A New, Efficient Method for the Synthesis of Bisindolylmaleimides", *J. Org. Chem.*, 1998, 63, 6053-6058.
Faul et al., "A New One Step Synthesis of Maleimides by Condensation of Glyoxylate Esters with Acetamides", *Tetrahedron Letters*, 1999, 40, 1109-1112.

(Continued)

*Primary Examiner* — D Seaman
*Assistant Examiner* — Niloofar Rahmani
(74) *Attorney, Agent, or Firm* — Viksnins Harris & Padys PLLP

(57) ABSTRACT

The present invention relates to a compound of formula (I) wherein $R^1$ is H, $C_1$-$C_6$-alkyl, phenyl-$C_1$-$C_4$-alkyl or phenyl, $R^2$ is a phenyl group which is substituted with 2 or 3 $C_1$-$C_6$-alkoxy groups and $R^3$ is indolyl or azaindolyl which may carry one or two substituents independently selected from $C_1$-$C_6$-alkyl, $C_1$-$C_6$-alkoxy, phenyl, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S and heterocyclyl with 5 or 6 ring atoms containing 1 or 2 heteroatoms which are independently selected from O, N, and S and the physiologically acceptable salts thereof as well as the physiologically acceptable solvates of the compounds of formula 1 and of the salts thereof. The compounds of formula (I) are suitable for controlling angiogenesis.

(I)

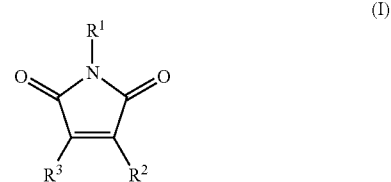

12 Claims, No Drawings

OTHER PUBLICATIONS

Hands et al., "A Convenient Method for the Preparation of 5-, 6- and 7-Azaindoles and Their Derivatives", *Synthesis*, 1996, 7, 877-882.

Mahadevan et al., "Synthesis of Pyrrolopyridines (Azaindoles)", *J. Heterocycl. Chem.*, 1992, 29, 359-367.

Okauchi et al., "A General Method for Acylation of Indoles at the 3-Position with Acyl Chlorides in the Presence of Dialkylaluminum Chloride", *Organic Letters*, 2000, 2 (10), 1485-1487.

O'Neill et al., "Design, synthesis and biological evaluation of novel 7-azaindolyl-heteroaryl-maleimides as potent and selective glycogen synthase kinase-3β (GSK-3β) inhibitors", *Bioorg. Med. Chem.*, 2004, 12, 3167-3185.

Peifer et al., "Profile and Molecular Modeling of 3-(Indole-3-yl)-4-(3,4,5-trimethoxyphenyl)-1 H-pyrrole-2,5-dione (1) as a Highly Selective VEGF-R2/3 Inhibitor", *J. Med. Chem.*, 2006, 49, 7549-7553.

Peifer et al., "Design, Synthesis, and Biological Evaluation of 3,4-Diarylmaleimides as Angiogenesis Inhibitors", *J. Med. Chem.*, 2006, 49, 1271-1281.

Peifer et al., "A novel quantitative chick embryo assay as an angiogenesis model using digital image analysis", *Anticancer Res.*, 2004, 24, 1545-1552.

Tanaka et al., "Synthesis of anilino-monoindolylmaleimides as potent and selective PKCβ inhibitors", *Bioorganic & Medicinal Chem. Lett.*, 2004, 14, 5171-5174.

Tholander et al., "Syntheses of 6,12-Disubstituted 5,11-Dihydroindolo[3,2-b]carbazoles, Including 5,11-Dihydroindolo[3,2-b]carbazole-6,12-dicarbaldehyde, an Extremely Efficient Ligand for the TCDD (Ah) Receptor", *Tetrahedron* 1999, 55 (43), 12577-12594.

Xu et al., "Synthesis and cytotoxicity of indolopyrrolemaleimides", *Chem. Pharm. Bull.* (Tokyo), 2007, 55, 1302-1307.

Zhang et al., "A General Method for the Preparation 4- and 6-Azaindoles", *J. Org. Chem.*, 2002, 67, 2345-2347.

Zhang et al., "An Effective Procedure for the Acylation of Azaindoles at C-3", *J. Org. Chem.*, 2002, 67, 6226-6227.

Zhang et al., "Novel indolylindazolylmaleimides as inhibitors of protein kinase C-β: synthesis, biological activity, and cardiovascular safety", *J. Med. Chem.*, 2005, 48, 1725-1728.

\* cited by examiner

3-(INDOLYL)-4-ARYLMALEIMIDE DERIVATIVES AND THEIR USE AS ANGIOGENESIS INHIBITORS

RELATED APPLICATIONS

This application is a National Stage application under 35 U.S.C. §371 and claims the benefit of priority of International Application No. PCT/EP2005/013126 having an International Filing Date of Dec. 7, 2005, which claims the benefit of priority of European Application Serial No. 04029069.4 filed on Dec. 8, 2004.

The present invention relates to 3-(indolyl)-4-arylmaleimide derivatives, pharmaceutical compositions containing them and their use as angiogenesis inhibitors.

Angiogenesis is a morphogenetic process which relates to the formation of new blood vessels from the endothelial cells of already existing capillary vessels. A number of pathological events in humans have been found to be associated with angiogenesis. Angiogenetic processes are pathologically responsible inter alia in rheumatoid arthritis, psoriasis, ischemia and malignant diseases. The occurrence of angiogenesis in connection with cancer and neoplasms, in particular in connection with tumor invasion and metastases formation, is remarkable. Therefore, angiogenesis inhibitors are contemplated as potential therapeutic agents in the treatment of solid tumors for which no effective therapies are known so far, such as bronchial carcinoma, mamma carcinoma, prostate carcinoma, glioblastoma, Karposi sarcoma, melanoma, lymphoma and multiple myeloma.

Many key functions in the angiogenetic process are controlled by protein kinases which therefore can be considered as signal integrators. Essential angiogenesis factors, such as Epidermal Growth Factor (EGF), Platelet Derived Growth Factor (PDGF), Fibroblast Growth Factor (FGF) and Vascular Endothelial Growth Factor (VEGF) mediate their effects by means of phosphorylations via thyrosine kinases. The development of selective kinase inhibitors is therefore of particular relevance.

WO 02/38561 discloses kinase inhibitors of the formula

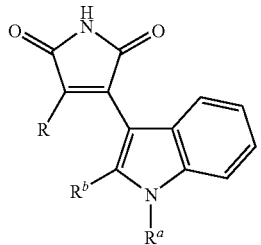

wherein R is an aryl radical such as a hydroxy substituted phenyl group.

Compounds of similar structure and having a comparable effect or other pharmacological activity are disclosed in EP 328 026 A, WO 02/10158, WO 03/057202, WO 03/095452, WO 03/103663, WO 95/07910, WO 00/38675, WO 97/34890, WO 91/13071, EP 384 349 A, EP 540 956, EP 1 224 932 A, WO 00/021927, and Bioorganic & Medicinal Chemistry Letters 14 (2004), 3245-3250.

The present invention relates to compounds of formula I:

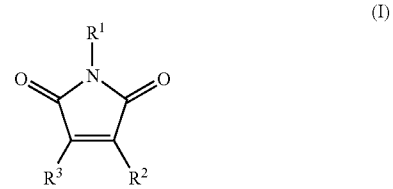

wherein
$R^1$ is H, $C_1$-$C_6$-alkyl, phenyl-$C_1$-$C_4$-alkyl or phenyl;
$R^2$ is a phenyl group which is substituted with 2 or 3 $C_1$-$C_6$-alkoxy groups, and
$R^3$ is indolyl or azaindolyl which may carry one or two substituents independently selected from $C_1$-$C_6$-alkyl, $C_1$-$C_6$-alkoxy, phenyl, OH, halogen, $NH_2$, $C_1$-$C_6$-alkylamino, di-$C_1$-$C_6$alkylamino, heteroaryl with 5 or 6 ring atoms containing 1 or 2 heteroatoms which are independently selected from O, N, and S and heterocyclyl with 5 or 6 ring atoms containing 1 or 2 heteroatoms which are independently selected from O, N, and S and
the physiologically acceptable salts thereof as well as the solvates of the compounds of formula I and of the salts thereof.

The term "alkyl", "alkoxy", "alkylamino" etc. includes linear or branched alkyl groups having 1 to 6 and preferably 1 to 4 carbon atoms. Examples for alkyl groups are methyl, ethyl, n-propyl, i-propyl, n-butyl, sec-butyl, iso-butyl, t-butyl, n-pentyl or n-hexyl. Examples for alkoxy groups are methoxy, ethoxy, n-propoxy, isopropoxy, n-butoxy.

Halogen means F, Cl, Br and I, preferably F and Cl.

Heteroaryl means a 5- or 6-membered aromatic ring having 1 or 2 heteroatoms selected from O, N. and S. Examples for heteroaryl are thienyl, furyl, imidazolyl, pyrazolyl, thiazolyl, oxazolyl, pyridyl or pyrimidyl.

Heterocyclyl means a 5- or 6-membered saturated or unsaturated, non-aromatic ring having 1 or 2 heteroatoms selected from O, N, and S. Examples for heterocyclyl are pyrrolidinyl, tetrahydrofuranyl, imidazolinyl, imidazolidinyl, piperidinyl, morpholinyl.

Physiologically acceptable salts of the compounds of formula I include acid addition salts with inorganic acids, such as hydrochloric acid, sulfuric acid, or phosphoric acid, or with organic acids, in particular carboxylic acids, such as acetic acid, tartaric acid, lactic acid, citric acid, maleic acid, amygdalic acid, ascorbic acid, fumaric acid, gluconic acid or sulfonic acids, such as methane sulfonic acid, benzene sulfonic acid and toluene sulfonic acid.

Physiologically acceptable solvates are in particular hydrates.

An embodiment of the present invention includes compounds of formula (I) wherein $R^2$ is a group having the formula

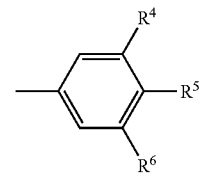

wherein two of the radicals $R^4$, $R^5$ and $R^6$ are $C_1$-$C_6$-alkoxy and the third of said radicals is H or $C_1$-$C_6$-alkoxy. Preferably, $R^4$ and $R^5$ are $C_1$-$C_6$-alkoxy and $R^6$ is hydrogen or $R^4$, $R^5$ and $R^6$ are $C_1$-$C_6$-alkoxy.

A further embodiment of the present invention includes compounds of formula (I)
wherein $R^3$ is selected from:

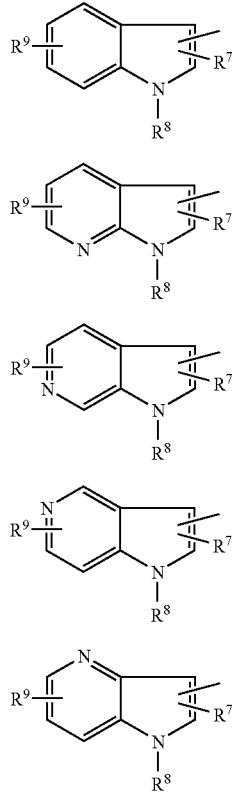

a)

b)

c)

d)

e)

wherein $R^7$ is H, $C_1$-$C_6$-alkyl or phenyl, $R^8$ is H, $C_1$-$C_6$-alkyl or phenyl and $R^9$ is H, $C_1$-$C_6$-alkyl, $C_1$-$C_6$-alkoxy, OH, halogen, $NH_2$, $C_1$-$C_6$-alkylamino, di-$C_1$-$C_6$-alkylamino, heteroaryl with 5 or 6 ring atoms containing 1 or 2 heteroatoms which are independently selected from O, N, and S and heterocyclyl with 5 or 6 ring atoms containing 1 or 2 heteroatoms which are independently selected from O, N, and S, preferably H, $C_1$-$C_6$-Alkyl or $C_1$-$C_6$-Alkoxy.

The indolyl or azaindolyl group, for example groups (a) to (e) are preferably attached to the maleimide group via the 3-position of the indolyl or azaindolyl group.

An embodiment of the present invention includes compounds of formula (Ia):

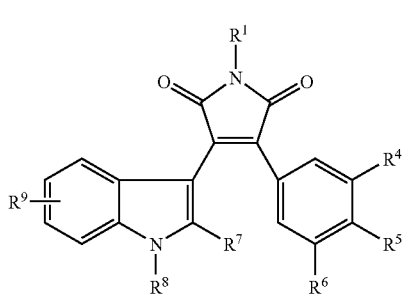

(Ia)

wherein $R^1$, and $R^4$ to $R^9$ have the meanings given above.

A further embodiment of the present invention includes compounds of formula (Ib):

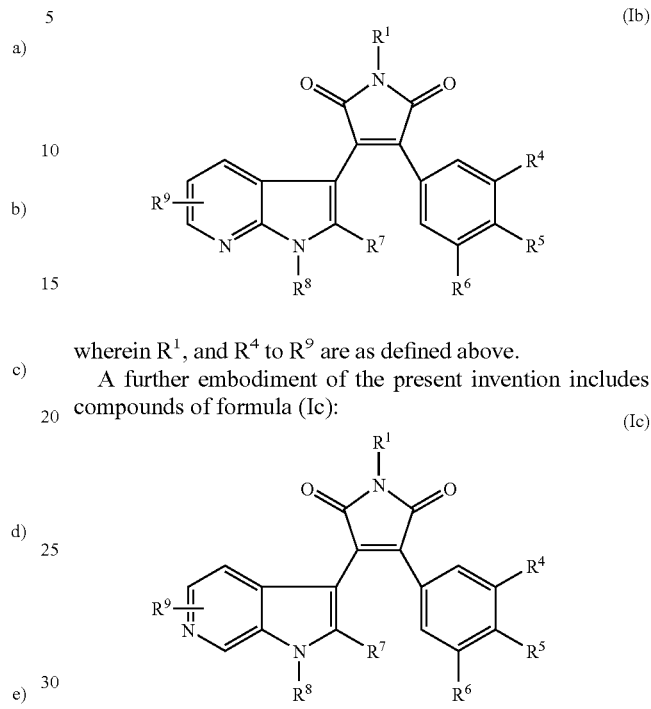

(Ib)

wherein $R^1$, and $R^4$ to $R^9$ are as defined above.

A further embodiment of the present invention includes compounds of formula (Ic):

(Ic)

wherein $R^1$, and $R^4$ to $R^9$ are as defined above.

A further embodiment of the present invention includes compounds of formula (Id):

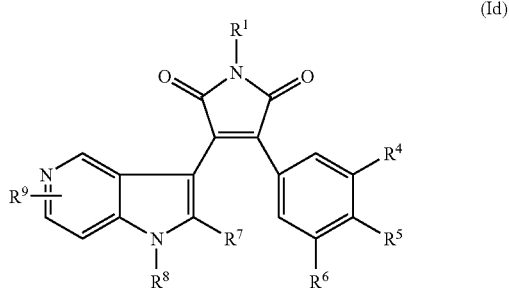

(Id)

wherein $R^1$, and $R^4$ to $R^9$ are as defined above.

A further embodiment of the present invention includes compounds of formula (Ie):

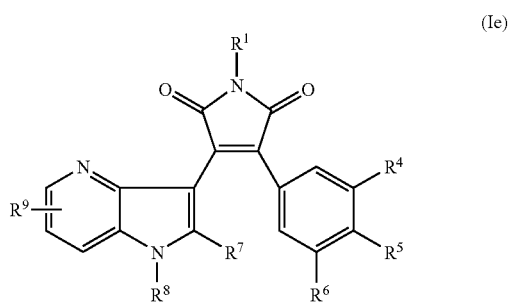

(Ie)

wherein $R^1$, and $R^4$ to $R^9$ are as defined above.

According to a further embodiment, $R^1$, $R^7$, $R^8$ and $R^9$ are independently of each other H or $C_1$-$C_6$-alkyl, and in particular, $R^1$, $R^7$, $R^8$, and $R^9$ are H.

The compounds of the present invention can be prepared according to known methods, for example according to the methods, which are disclosed in WO 02/38561, EP 328 026 and WO 03/095452. For the purposes of the present invention a modified procedure reported in *Tetrahedron Letters* (1999) 40: 1109-1112 has been proven to be particularly efficient. This procedure can be illustrated by the following reaction sequence:

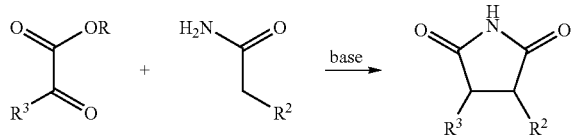

An indole glyoxyl ester is reacted with a phenyl acetamide derivative in a one-pot reaction in an inert solvent in the presence of a strong base. Preferably an ether is used as an inert solvent, such as tetrahydrofurane or dioxane. As a base potassium t-butoxide can for example be used. The water formed during the reaction is removed, for example by using a molecular sieve. The phenyl acetamides used as starting material are readily available from the corresponding acetic acids which are converted to the acid chloride and hydrolyzed with ammonia. The indole glyoxyl esters (R=methyl, ethyl) were synthesized by Friedel-Crafts-type acylation of the corresponding indole derivative with methyl or ethyl oxalyl chloride, cf. *Tetrahedron* 1999, 55 (43), 12577-12594. The corresponding azaindole glyoxyl esters can be prepared according to the method reported in *J. Org. Chem.* 2002, 67, 6226-6227 or by Friedel-Crafts acylation in the presence of dialkyl aluminium chloride, cf. *Organic Letters* (2000) vol. 2, no. 10, 1485-1487. The 4- and 6-azaindole starting compounds can be prepared by reacting 2-chloro-3-nitropyridine or 3-nitro-4-chloropyridine with vinyl magnesium bromide to give the 7-chloro-substituted 4- or 6-azaindole. The chloro substituent is then removed by catalytic hydrogenation. Said reactions are carried out as described in *J. Org. Chem.* 67, 2345-2347 (2002) and *J. Heterocycl. Chem.* 29, 359-363 (1992).

The 5- and 7-azaindole starting compounds can be prepared by reacting 2- or 4-aminopyridine with di-tert-butyldicarbonate to 2- or 4-t-butoxycarbonylaminopyridine which is then reacted with methyl iodide and dimethylformamide in the presence of t-butyl lithium. The obtained product is then treated with a strong acid to give 5- or 7-azaindole. Said reactions are described in *Synthesis* 7, 877-882 (1996).

The compounds of the present invention are effective angiogenesis inhibitors. They can be used to control angiogenesis and/or vascular dysfunction. Pathological angiogenesis or vascular dysfunction is associated with a large number of disorders such as:

| | |
|---|---|
| Blood vessels: | Atherosclerosis, haemangioma, vascular deformity; |
| Skin, mucosa: | Granuloma, hair growth, Karposi sarcoma, neoplasms, psoriasis, decubitus, gastrointestinal ulcera; |
| Uterus, placenta: | Follicular cysts, endiometrosis, neoplasms; |
| Heart, skeleton muscles: | Ischemiae; |
| Bones, joints: | Rheumatoid arthritis, synovitis, bone and cartilage destruction, osteomyelitis, pannus growth, cancer; |
| Liver, kidney, lung (and other epithelial layers): | Hepatitis, pneumonia, glomerulonephritis, polyps, asthma, cancer; |
| Brain, nerves, eyes: | Retinopathies, leucomalazia, cancer; |
| Lymphatic vessels: | Tumor metastases (lymphangiogenesis), proliferative lymphoma. |

The compounds of the present invention can be used for the treatment or prevention of the above-mentioned disorders and in particular solid tumors, psoriasis, granuloma, atherosclerotic plaques, diabetic retinopathy, neovascular glaucoma, wound healing, hypertrophy, haemangioma.

For use the compounds of the present invention can be incorporated into standard pharmaceutical dosage forms. Thus, the present invention also relates to pharmaceutical compositions comprising a pharmaceutically acceptable carrier and an amount therapeutically effective for control of angiogenesis and/or vascular dysfunction of a compound of formula (I) as above-defined. For example, they are useful when administered in systemic or local, oral or parenteral applications and for this purpose are combined with the usual pharmaceutical excipients, diluents and adjuvants, e.g., organic and inorganic inert carrier materials such as water, gelatin, lactose, starch, magnesium stearate, talc, vegetable oils, gums, polyalkyleneglycols, etc. These pharmaceutical preparations can be employed in a solid form, e.g., as tablets, capsules, and especially in combination with or for admixture with a palatable food item suitable for mammals; or they can be administered in liquid form, e.g., as solutions and elixirs. Pharmaceutical excipients and adjuvants which can be added to include preservatives, antioxidants, antimicrobial agents and other stabilizers; wetting, emulsifying, and suspending agents, and anticaking compounds; fragrance and coloring additives; compositions for improving compressibility, or to create a delayed-, sustained-, or controlled-release of the active ingredient; and various salts to change the osmotic pressure of the pharmaceutical preparation or to act as buffers.

The therapeutically effective amount of a compound of Formula (I) as defined may be administered systemically to said mammal, wherein said systemic administration comprises: (1) injection or infusion into suitable body tissues or cavities of a pharmaceutical composition containing said compound in suitable liquid form such as aqueous solutions, emulsions or suspensions for intraarterial, intra- or transdermal (including subcutaneous) and most commonly intramuscular or intravenous delivery thereof; or for serving as a depot for delivery thereof; (2) instillation into suitable body tissues or cavities of a pharmaceutical composition containing said compound in suitable solid form, e.g., comprising a matrix of bio-compatible and bio-erodible materials in which particles of a compound of Formula (I) are dispersed for serving as a solid implant composition for delayed-, sustained-, and/or controlled-release delivery thereof; or (3) ingestion or administration of a pharmaceutical composition containing said compound in suitable solid or liquid form for transdermal delivery thereof, for instance a transdermal patch or a subepidermal (subcuticular) implant, for peroral delivery thereof.

The dosage forms described herein may be formulated so as to provide controlled-, sustained-, and/or delayed release of the active ingredient from said dosage form.

Preferred peroral dosage forms for systemic administration are solids, e.g., palatable oral compositions such as fast dissolving palatable wafers, tablets, capsules, caplets, etc., and liquids, e.g., solutions, suspensions, emulsions, etc. Pharmaceutical compositions of special types suitable for oral administration to mammals may be used, and include, but are not limited to such items as an oral paste to be delivered to the back of the tongue of the mammal being treated, a granular form to be delivered through incorporation in the mammal's food, and a chewable form wherein the active ingredient is consumed along with the palatable chew, or a chewable form which may deliver the active ingredient by leaching from the body of the chew which is not consumed, during mastication by the mammal being treated. Tablets and capsules are preferred dosage forms.

Said therapeutically effective amount of a compound of Formula (I) as defined may also be administered locally to said mammal, wherein said local administration comprises: (1) injection or infusion into a local site affected with abnormal angiogenesis and/or vascular dysfunction of a pharmaceutical composition containing said compound of formula (I) in suitable liquid form for delivery thereof, including components which provide delayed-release, controlled-release, and/or sustained-release of said compound into said local site; or for serving as a depot for delivery thereof wherein said composition provides storage of said compound and thereafter delayed-, sustained-, and/or controlled-release thereof; or (2) instillation of a pharmaceutical composition containing said compound in suitable solid form for serving as a solid implant for delivery thereof, said composition optionally providing delayed-, sustained-, and/or controlled-release of said compound to said local site.

The therapeutically effective amount of the compound of Formula (I), is administered to a mammal to be treated in an amount expressed as milligrams per kilogram of body weight of said mammal, per day: "mg/kg/day". The dose, i.e., the therapeutically effective amount of a compound of Formula (I) will usually range from about 0.1 mg/kg/day to about 20.0 mg/kg/day, preferably from about 0.1 mg/kg/day to about 12.0 mg/kg/day, more preferably from about 0.5 mg/kg/day to about 10.0 mg/kg/day, and most preferably from about 0.5 mg/kg/day to about 8.0 mg/kg/day. It is necessary for the skilled artisan, not only to determine the preferred route of administration and the corresponding dosage form and amount, but said artisan must also determine the dosing regimen, i.e., the frequency of dosing. In general terms it is most likely that the choice will be between once-a-day (s.i.d.) dosing and twice-a-day (b.i.d.) dosing, and that the former will provide more rapid and profound therapy, while the latter will provide less profound but more sustained therapy.

The method of the present invention can be further defined to comprise two basic steps: (I) establishing the status of a candidate mammal as presently or prospectively being in a condition of pathological angiogenesis and/or vascular dysfunction, thereby confirming that said mammal is in need of such treatment; and thereupon (II) treating or preventing said condition by administering to said mammal an amount therapeutically effective for treating or preventing said disorder of a compound of Formula (I).

The antiangiogenic activity of the compounds of the present invention was determined by the following assays:

Chick Embryo Assay as In Vivo Angiogenesis Model.

The assay was basically performed as described in Anticancer Research 24: 1545-1552 (2004). Test compounds were dissolved in dimethylsulfoxide (DMSO) and used as stock solution. For the preparation of agarose pellets, the stock solution was mixed with 2% agarose solution at 80° C. and 10 µl pellets were produced (final content 5-100 µg).

Fertilised chicken eggs (White leghorn) were incubated at 37.5° C. and 62% relative humidity in an automatically turning egg incubator (Ehret). After 70 hours of incubation and removal of 8 ml albumin, a window was opened in the shell to uncover the developing germination layer. The window was sealed with transparent tape, the eggs returned to the incubator and stored at 90% relative humidity without turning. At 75-h incubation time the angiogenic experiment was initiated (start-time: 0 h) and 15 agarose pellets were placed on the area vasculosa preparations. After 24 h, images of the control and sample-treated areas were taken. Images were digitised via Leica QWin™-Software and the angiogenic response was measured using the automatic image analysis system programmed in a routine. The digitised images were analysed for total, major (capillaries with a diameter of more than 50 µm) and minor blood vessel areas using the customized image analysis software Leica QWin™ (Leica Microsystems Bensheim, Germany). Calculated data were sent automatically via Dynamic Data Exchange to an Excel table and processed statistically. An antiangiogenic response due to agent-treated samples was considered positive if the mean of minor blood vessel area showed >20% inhibition compared to control samples. Differences between treated and control samples were evaluated using Student's t-test.

Tubulin Polymerisation Assay

The antimitotic activity of the compounds was determined using a slightly modified version of the turbidimetric tubulin assembly in vitro assay described by Gaskin et al., *J. Mol. Biol.* 1974, 89(4), 737-755).

In this assay, the assembly of microtubule protein isolated from porcine brain is monitored in vitro in presence of effectors. The principle is based on the fact that microtubules increase the turbidity of the test solution, compared to unpolymerized tubulin dimers. The degree of assembly is measured by detecting the change in absorbance of the test solution compared to a control.

The measurements were performed at 360 nm with a Uvikon 930 UV spectrophotometer (Kontron Instruments) equipped with a multicell holder connected to a thermostat. The influence of the test substances on tubulin assembly (protein concentration 1 mg/ml) was determined by comparing the change of absorption to a control without effectors. Assembly was performed for 20 min in a PIPES (piperazine-1,4-bis-(2-ethanesulfonic acid)) buffer containing 10 mM GTP at pH 6.8 and a temperature of 37° C. To exclude protein denaturation and to check reversibility of assembly, the measurement was continued for additional 20 min during decreasing the temperature to 4° C. that should shift turbidity to the pre-assembly level.

Selectivity Profiling of Compounds in Two Concentrations Using Protein Kinases

Recombinant protein kinases: The inhibitory profile of compounds was determined using the following 12 protein kinases: CDK1/CyclinB, CDK2/CyclinE, CDK4/CyclinD1, CDK6/CyclinD1, PKC-alpha, PKC-gamma, PKC,epsilon, PKC-iota, EGF-R, ERBB2, TIE2, VEGF-R2.

All protein kinases were expressed in Sf9 insect cells as recombinant GST-fusion proteins or His-tagged proteins by means of the baculovirus expression system. Except for PKC-alpha (mouse), PKC-epsilon (mouse) and PKC-gamma (rat), human cDNAs were used for the expression of the protein kinases. Kinases were purified by affinity chromatography using either GSH-agarose (Sigma) or Ni-NTH-agarose (Qiagen). The purity and identity of each kinase was checked by SDS-PAGE/silver staining and by western blot analysis with specific antibodies.

Protein kinase Assay: A proprietary protein kinase assay ($^{33}$PanQinase® Activity Assay) was used for measuring the kinase activity of the 12 protein kinases. All kinase assays were performed in 96-well FlashPlates™ from Perkin Elmer/ NEN (Boston, Mass., USA) in a 50 µl reaction volume.

The assay for all enzymes (except for the PKC assay, see below) contained 60 mM HEPES-NaOH, pH 7.5, 3 mM $MgCl_2$, 3 mM $MnCl_2$, 3 µM Na-orthovanadate, 1.2 mM DTT, 50 µg/ml $PEG_{20000}$, 1 µM [γ-$^{33}$P]-ATP (approx. 5×10$^5$ cpm per well), recombinant protein kinase (50-400 ng) and depending from the kinase, the following substrate proteins: Rb-CTF (CDK1, CDK4, CDK6), poly(Glu,Tyr)4:1 (EGF-R, ERBB2, TIE2, VEGF-R2), Histone H1 (CDK2).

The PKC assay contained 60 mM HEPES-NaOH, pH 7.5, 1 mM EDTA, 1.25 mM EGTA, 5 mM $MgCl_2$, 1.32 mM $CaCl_2$, 5 µg/ml Phosphatidylserine, 1 µg/ml 1,2 Dioleyl-glycerol, 1.2 mM DTT, 50 µg/ml $PEG_{20000}$, 1 µM [γ-$^{33}$P]-ATP (approx. 5×10$^5$ cpm per well), recombinant protein kinase (20-100 ng) und Histone H1 as substrate.

The compounds were tested at a concentration of 10 µM and 100 µM in singlicate. The final DMSO concentration in the assay was 1%.

The reaction cocktails were incubated at 30° C. for 80 min. The reaction was stopped with 50 µl of 2% (v/v) $H_3PO_4$, plates were aspirated and washed two times with 200 µl of 0.9% (w/v) NaCl. Incorporation of $^{33}P_i$ was determined with a microplate scintillation counter (Microbeta Trilux, Wallac). All assays were performed with a Beckman Coulter/Sagian robotic system.

For each compound inhibition was calculated as percentage relative to control values without test compound.

EXAMPLES

Infrared spectra were recorded on a Perkin Elmer 1310 infrared spectrophotometer. 1H (300 MHz, digital resolution 0.3768 Hz) and 13C (75 MHz, digital resolution 1.1299 Hz) NMR were recorded on a Bruker AC 300: the data are reported as follows: chemical shift in ppm from $Me_4Si$ as external standard, multiplicity and coupling constant (Hz). EI-Mass spectra were recorded on a Varian MAT 311A (70 eV) and FD-Mass spectra on a MAT-95 (Finnigan). For clarity only the highest measured signal is given for FD-mass spectra. Elemental analyses were performed on an Elemental Analyzer Carlo Erba Strumentazione Mod. 1106. Combustion analyses agreed with the calculated data within ±0.4 unless otherwise stated. Melting points/decomposition temperatures were determined on a Büchi apparatus according to Dr. Tottoli and are uncorrected. Where appropriate, column chromatography was performed for crude precursors with Merck silica gel 60 (0.063-0.200 mm) or Acros organics silica gel (0.060-0.200 mm; pore diameter ca. 60 nm). Column chromatography for test compounds was performed using a MPLC-System B-680 (Büchi) with Merck silica gel 60 (0.015-0.040 mm). The progress of the reactions was monitored by thin-layer chromatography (TLC) performed with Merck silica gel 60 F-245 plates. Where necessary reactions were carried out in a nitrogen atmosphere using 4 Å molecular sieves. All reagents and solvents were obtained from commercial sources and used as received (THF was used after distillation over K/benzophenone).

General Procedure for the Preparation of 3-phenyl-4-indolylmaleimides

A modified procedure of Faul et al., *Tetrahedron Letters* 1999, 40, 1109-1112 and *J. Org. Chem.* 1998, 63, 6053-6058 was used. A stirred solution of the corresponding phenylacetamide (1 equiv.) and indolylmethyl- or indolylethylglyoxylate (24 equiv.) in dry THF containing 15 g molecular sieve (4 Å) was cooled to 0° C. under nitrogen. At this temperature 1.0 M KOBu$^t$ in $^t$BuOH (3.0 equiv.) was added via septum and the mixture was allowed to warm to room temperature. After stirring over night, the reaction was again cooled to 0° C. and quenched with saturated $NH_4Cl$-solution. The residue was filtered, extracted with ethyl acetate and the organic phase dried over $Na_2SO_4$, then concentrated and purified by column chromatography.

Example 1

3-(Indole-3-yl)-4-(3,4,5-trimethoxyphenyl)-1H-pyrrole-2,5-dione

The general procedure was followed using indole-3-ethylglyoxylate (1.6 g, 7.38 mmol); 3,4,5-trimethoxyphenylacetamide (1.2 g, 5.33 mmol) and 1.0 M KOBu$^t$ (20 ml, 20.0 mmol). Purification was achieved by column chromatography (ethyl acetate/hexanes 1/1) to yield the title compound (1.08 g, 54%) as yellow crystals. mp=227° C. $^1$H NMR (DMSO-d$_6$), 300 MHz, δ [ppm]=3.37 (s, 6H, OCH$_3$); 3.66 (s, 3H, OCH$_3$); 6.36 (d, 1H); 6.73 (m, 3H); 7.08 (t, 1H); 7.43 (d, 1H); 7.98 (m, 1H); 11.05 (s, 1H, NH); 11.91 (s, 1H, NH). EI-MS (m/z): 378.8 (M$^+$).

5,6,7-Trimethoxy-1,2,3,8-tetrahydro-benzo[a]pyrrolo[3,4-c]carbazol-1,3-dione

The product was isolated by column chromatography (ethyl acetate/hexanes 4/6) from the reaction mixture obtained above as bright yellow crystals (151 mg, 8%). mp=272° C. $^1$H NMR (DMSO-d$_6$), 300 MHz, δ [ppm]=3.95 (s, 3H, OCH$_3$); 3.97 (s, 3H, OCH$_3$); 4.18 (s, 3H, OCH$_3$); 7.33 (t, 1H); 7.50 (t, 1H); 7.87 (d, 1H); 8.24 (s, 2H); 8.91 (d, 1H); 11.08 (s, 1H, NH); 11.89 (s, 1H, NH). EI-MS (m/z): 376.7 (M$^+$).

Example 2

3-(Indole-3-yl)-4-(3,4-dimethoxyphenyl)-1H-pyrrole-2,5-dione

The general procedure was followed using indole-3-ethylglyoxylate (0.86 g, 3.94 mmol); 3,4-dimethoxyphenylacetamide (0.70 g, 3.59 mmol) and 1.0 M KOBu$^t$ (10 ml, 10.0 mmol). Purification was achieved by column chromatography (ethyl acetate/hexanes 1/1) to yield the title compound (0.51 g, 41%) as yellow crystals. mp=210° C. $^1$H NMR (DMSO-d$_6$), 300 MHz, δ [ppm]=3.24 (s, 3H, OCH$_3$); 3.74 (s, 3H, OCH$_3$); 6.43 (d, 1H); 6.74 (t, 1H); 6.93 (m, 2H); 7.06 (t, 1H); 7.14 (m, 1H); 7.92 (m, 1H); 10.99 (s, 1H, NH); 11.86 (s, 1H, NH). EI-MS (m/z): 348.0 (M$^+$).

Example 3

3-(5-Methoxyindole-3-yl)-4-(3,4,5-trimethoxyphenyl)-1H-pyrrole-2,5-dione

The general procedure was followed using 5-methoxyindole-3-ethylglyoxylate (1.5 g, 6.07 mmol); 3,4,5-trimethoxyphenylacetamide (1.2 g, 5.33 mmol) and 1.0 M KOBu$^t$ (10 ml, 10.0 mmol). Purification was achieved by column chromatography (ethyl acetate/hexanes 4/6) to yield the title compound (1.72 g, 70%) as red crystals. mp=268° C. $^1$H NMR (DMSO-d$_6$), 300 MHz, δ [ppm]=3.24 (s, 3H, OCH$_3$); 3.42 (s, 6H, OCH$_3$); 3.66 (s, 3H, OCH$_3$); 5.84 (s, 1H); 6.67-6.71 (m, 3H); 7.32 (d, 1H); 7.97 (s, 1H); 11.02 (s, 1H, NH); 11.81 (s, 1H, NH). FD-MS (m/z): 410.1 (M$^+$+1), 408.1 (M$^+$).

11-Methoxy-5,6,7-trimethoxy-1,2,3,8-tetrahydro-benzo[a]pyrrolo[3,4-c]carbazol-1,3-dione The product was isolated by column chromatography (ethyl acetate/hexanes 4/6) from the above reaction mixture as red crystals (440 mg, 18%). mp=290° C. $^1$H NMR (DMSO-d$_6$), 300 MHz, δ [ppm]=3.88 (s, 3H, OCH$_3$); 3.95 (s, 3H, OCH$_3$); 3.98 (s, 3H, OCH$_3$); 4.18 (s, 3H, OCH$_3$); 7.15 (m, 1H); 7.78 (d, 1H); 8.25 (s, 1H); 8.47 (m, 1H); 11.07 (s, 1H, NH); 11.78 (s, 1H, NH). FD-MS (m/z): 408.0 (M$^+$+2).

Example 4

3-(1-Methylindole-3-yl)-4-(3,4,5-trimethoxyphenyl)-1H-pyrrole-2,5-dione

The general procedure was followed using 1-methylindole-3-methylglyoxylate (0.65 g, 3.0 mmol); 3,4,5-trimethoxyphenylacetamide (0.69 g, 3.06 mmol) and 1.0 M KOBu$^t$ (5 ml, 5.0 mmol). Purification was achieved by column chromatography (ethyl acetate/hexanes/CH$_2$Cl$_2$ 3.5/6/0.5) to yield the title compound (0.74 g, 62%) as red crystals. mp=187° C. $^1$H NMR (DMSO-d$_6$), 300 MHz, δ [ppm]=3.38 (s, 3H, CH$_3$); 3.66 (s, 6H, OCH$_3$); 3.90 (s, 3H, OCH$_3$); 6.72 (d, 1H); 6.72 (s, 2H); 6.79 (t, 1H); 7.15 (t, 1H); 7.50 (d, 1H); 8.04 (s, 1H); 11.06 (s, 1H, NH). EI-MS (m/z): 392.2 (M$^+$).

5,6,7-Trimethoxy-8-methyl-1,2,3,8-Tetrahydro-benzo[a]pyrrolo[3,4-c]carbazol-1,3-dion The product was isolated by column chromatography (ethyl acetate/hexanes 4/6) from the above reaction mixture as pale red crystals (60 mg, 5%). mp=185° C. $^1$H NMR (DMSO-d$_6$), 300 MHz, δ [ppm]=3.72 (s, 3H); 3.98 (s, 3H); 3.99 (s, 3H); 4.04 (s, 3H); 7.40 (t, 1H); 7.60 (t, 1H); 7.74 (d, 1H); 8.34 (s, 1H); 8.99 (d, 1H); 11.12 (s, 1H, NH). FD-MS (m/z): 390.2 (M$^+$).

Example 5

3-(2-Methylindole-3-yl)-4-(3,4,5-trimethoxyphenyl)-1H-pyrrole-2,5-dione

The general procedure was followed using 2-methylindole-3-ethylglyoxylate (1.60 g, 6.9 mmol); 3,4,5-trimethoxyphenylacetamide (1.2 g, 5.33 mmol) and 1.0 M KOBu$^t$ (20 ml, 20.0 mmol). Purification was achieved by column chromatography (ethyl acetate/hexanes 1/1) to yield the title compound (0.91 g, 44%) as red crystals. mp=266° C. $^1$H NMR (DMSO-d$_6$), 300 MHz, δ [ppm]=2.25 (s, 3H, CH$_3$); 3.35 (s, 6H, OCH$_3$); 3.62 (s, 3H, OCH$_3$); 6.79 (m, 2H); 6.83 (s, 2H); 7.01 (m, 1H); 7.29 (d, 1H); 11.07 (s, 1H, NH); 11.53 (s, 1H, NH). EI-MS (m/z): 393.3 (M$^+$+1).

Example 6

3-(2-Phenylindole-3-yl)-4-(3,4,5-trimethoxyphenyl)-1H-pyrrole-2,5-dione

The general procedure was followed using 2-phenylindole-3-ethylglyoxylate (1.25 g, 4.26 mmol); 3,4,5-trimethoxyphenylacetamide (0.82 g, 3.06 mmol) and 1.0 M KOBu$^t$ (10 ml, 10.0 mmol). Purification was achieved by column chromatography (ethyl acetate/hexanes 1/1) to yield the title compound (0.82 g, 56%) as red crystals. mp=304° C. $^1$H NMR (DMSO-d$_6$), 300 MHz, δ [ppm]=3.34 (s, 6H, OCH$_3$); 3.60 (s, 3H, OCH$_3$); 6.88 (s, 2H); 6.70 (m, 2H); 7.14 (t, 1H); 7.32 (t, 1H); 7.43 (m, 3H); 7.54 (m, 2H); 11.09 (s, 1H, NH); 11.96 (s, 1H, NH). EI-MS (m/z): 455.2 (M$^+$).

Example 7

3-(Indole-2-yl)-4-(3,4,5-trimethoxyphenyl)-1H-pyrrole-2,5-dione

The general procedure was followed using indole-2-ethylglyoxylate (1.0 g, 4.61 mmol); 3,4,5-trimethoxyphenylacetamide (0.8 g, 3.0 mmol) and 1.0 M KOBu$^t$ (10 ml, 10.0 mmol). Purification was achieved by column chromatography (ethyl acetate/hexanes 1/1) to yield the title compound (1.12 g, 65%) as red crystals. mp=252° C. $^1$H NMR (DMSO-d$_6$), 300 MHz, δ [ppm]=3.68 (s, 6H, OCH$_3$); 3.75 (s, 3H, OCH$_3$); 6.87 (s, 2H); 6.98 (m, 2H); 7.14 (t, 1H); 7.53 (m, 2H); 11.04 (s, 1H, NH); 11.28 (s, 1H, NH). EI-MS (m/z): 378.7 (M$^+$).

Example 8

3-(7-Azaindol-3-yl)-4-(3,4,5-trimethoxyphenyl)-1H-pyrrole-2,5-dione

Aluminium chloride (50:25 mmol; 6.70 g) and 7-azaindole (10.16 mmol; 1.20 g) were stirred in 30 ml anhydrous methylene chloride at room temperature and under nitrogen atmosphere. After 30 minutes ethyl oxalylchloride was slowly added dropwise. The reaction mixture was stirred overnight and then carefully hydrolyzed with ethanol/ice. After addition of methylene chloride the organic layer was separated, washed with NaHCO$_3$ solution and water, dried over sodium sulfate and the solvent was removed. A yellow oily residue was obtained which solidified to a greenish-yellow powder, which was washed with cold diethyl ether to give ethyl 7-azaindol-3-glyoxylate (5.13 mmol; 50.5%) as light yellow powder.

MS FD m/z (rel. Int.)=219.7 (100%):
$^1$H-NMR CDCl$_3$, 200 MHz, δ[ppm]=1.46 (t, J=7.074 Hz, 3H); 4.47 (q, J=7.074 Hz, 2H); 7.35 (m, 1H); 8.47 (m, 1H); 8.74 (m, 2H); 13.50 (s, 1H, NH).

The general procedure was then followed using the above product (4.70 mmol; 1.03 g) and 3,4,5-trimethoxyphenylacetamide (2.98 mmol; 0.80 g) and 1.0 M KOBu$^t$ (10 ml, 10.0 mmol). Purification was achieved by column chromatography (petrol ether/ethyl acetate/isopropanol 7/2/1) to yield the title compound (0.76 g, 42.6%) as yellow crystals. mp=162° C. MS: m/z (rel. Int.)=379.1 (100%, M$^+$); 303.9 (20%); 288.9 (21%); $^1$H-NMR: DMSO-d$_6$, 300 MHz, d [ppm]=3.43 (s, 6H, OCH$_3$); 3.68 (s, 3H, OCH$_3$); 6.67 (m, 3H); 6.83 (m, 1H); 8.06 (m, 1H); 8.21 (m, 1H); 11.13 (s, 1H, Imid NH); 12.37 (s, 1H, 7-azaindol NH).

Example 9

3-(6-Azaindol-3-yl)-4-(3,4,5-trimethoxyphenyl)-1H-pyrrole-2,5-dione

Di-tert-butyldicarbonat (7 mmol, 1.5 g) and 4-(dimethylamino)pyridine (0.35 mmol, 0.04 g) were added to a stirred suspension of 6-azaindole-3-ethylglyoxylate (3.5 mmol, 0.76 g) in dichloromethane. After 2 hours the solvent was evaporated and the residue was purified by column chromatography (ethyl acetate/petrol ether 1/1) to yield N-Boc-6-azaindole-3-ethylglyoxylate (1.1 g, 100%) as white crystals. $^1$H NMR (CDCl$_3$), 300 MHz, δ [ppm]=9.43 (s, 1H); 8.93 (s, 1H); 8.56 (d, 1H, J=5.3 Hz); 8.26 (d, 1H, J=5.3 Hz); 4.44 (q, 2H, J=7.1

Hz); 1.72 (s, 9H); 1.44 (t, 3H, J=7.1 Hz). IR ν [cm$^{-1}$]=3110; 2971; 1758; 1739; 1660. FD-MS (m/z)=318.1 (M$^+$).

The general procedure was followed using the above product (3.1 mmol; 1 g) and 3,4,5-trimethoxyphenylacetamide (1.5 mmol; 0.4 g) and 1.0 M KOBu$^t$ (4.5 mmol; 4.5 ml). Purification was achieved by column chromatography (petrol ether/ethyl acetate/isopropanol 5/2/3). The obtained yellow oil was recrystallized from chloroform as yellow crystals. mp=244° C. $^1$H NMR (DMSO-d$_6$), 300 MHz, δ [ppm]=12.38 (s, 1H, NH); 11.16 (s, 1H, NH); 8.78 (s, 1H); 8.15 (s, 1H); 7.85 (d, 1H, J=5.2 Hz); 6.71 (s, 2H); 6.26 (d, 1H, J=5.2 Hz); 3.67 (s, 3H, OCH$_3$); 3.42 (s, 6H, OCH$_3$). IR ν [cm$^{-1}$]=1765; 1720; 1698; 1625. FD-MS (m/z): 379.3 (M$^+$).

Example 10

3-(5-Azaindol-3-yl)-4-(3,4,5-trimethoxyphenyl)-1H-pyrrole-2.5-dione

Di-tert-butyldicarbonat (7 mmol, 1.5 g) and 4-(dimethylamino)pyridine (0.35 mmol, 0.04 g) were added to a stirred suspension of 5-azaindole-3-ethylglyoxylate (3.5 mmol, 0.76 g) in dichloromethane. After 2 hours the solvent was evaporated and the residue was purified by column chromatography (ethyl acetate/petrol ether 1/1) to yield N-Boc-5-azaindole-3-ethylglyoxylate (1.1 g, 100%) as white crystals. $^1$H NMR (DMSO-d$_6$), 300 MHz, δ[ppm]=9.64 (s, 1H); 8.84 (s, 1H); 8.61 (d, 1H, J=5.8 Hz); 8.04 (d, 1H, J=5.8 Hz); 4.45 (q, 2H, J=7.2 Hz); 1.72 (s, 9H); 1.45 (t, 3H, J=7.2 Hz). IR ν [cm$^{-1}$]= 1758; 1733; 1670; 1540. FD-MS (m/z)=318.1 (M$^+$).

The general procedure was followed using the above product (3.1 mmol; 1 g) and 3,4,5-trimethoxyphenylacetamide (1.5 mmol; 0.4 g) and 1.0 M KOBu$^t$ (4.5 mmol; 4.5 ml). Purification was achieved by column chromatography (petrol ether/ethyl acetate/isopropanol 5/2/3). The obtained yellow oil was recrystallized from chloroform as yellow crystals. mp=240° C. $^1$H NMR (DMSO-d$_6$), 300 MHz, δ [ppm]=8.13 (d, 1H, J=5.6 Hz); 8.03 (s, 1H); 7.61 (s, 1H); 7.42 (d, 1H, J=5.6 Hz); 6.72 (s; 2H); 3.67 (s, 3H); 3.41 (s, 6H). IR ν [cm$^{-1}$]=1765; 1698; 1610. FD-MS (m/z): 379.3 (M$^+$).

The invention claimed is:

1. 3-(Indolyl)- or 3-(Azaindolyl)-4-phenylmaleimide derivatives of formula I

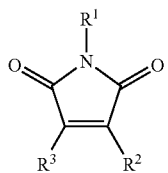

(I)

wherein
R$^1$ is H, C$_1$-C$_6$-alkyl, phenyl-C$_1$-C$_4$-alkyl or phenyl,
R$^2$ is a phenyl group which is substituted with 3 C$_1$-C$_6$-alkoxy groups and R$^3$ is selected from:

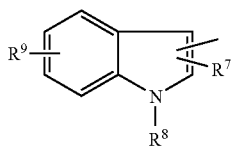

a)

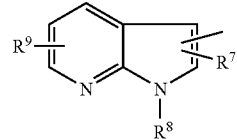

b)

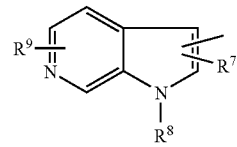

c)

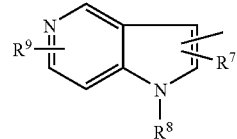

d)

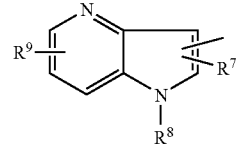

e)

wherein R$^7$ is H, C$_1$-C$_6$-alkyl or phenyl, R$^8$ is H, C$_1$-C$_6$-alkyl or phenyl and R$^9$ is H, C$_1$-C$_6$-alkyl, C$_1$-C$_6$-alkoxy, OH, halogen, NH$_2$, C$_1$-C$_6$-alkylamino, di-C$_1$-C$_6$-alkylamino, heteroaryl with 5 or 6 ring atoms containing 1 or 2 heteroatoms which are independently selected from O, N, and S and heterocyclyl with 5 or 6 ring atoms containing 1 or 2 heteroatoms which are independently selected from O, N, and S; and the physiologically acceptable salts thereof.

2. The compounds of claim 1, wherein R$^2$ is a group having the formula

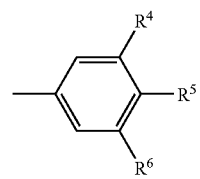

wherein R$^4$, R$^5$ and R$^6$ are C$_1$-C$_6$-alkoxy.

3. The compounds of claim 1 wherein R$^9$ is H, C$_1$-C$_6$-alkyl or C$_1$-C$_6$-alkoxy.

4. The compounds of claim 1, wherein R$^7$, R$^8$ and R$^9$ are H.

5. The compounds of claim 1, wherein R$^1$ is H.

6. The compounds of claim 1, wherein groups (a) to (e) are attached to the maleimide group via the 3-position of the indole group.

7. The compounds of claim 1 having formula Ia

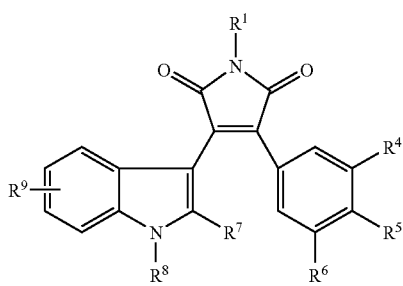

(Ia)

wherein $R^1$ is as defined in claim 1, $R^4$, $R^5$ and $R^6$ are $C_1$-$C_6$-alkoxy and $R^7$, $R^8$ and $R^9$ are as defined in any one of claim 1, 3 or 4.

8. The compounds of claim 1 having formula Ib

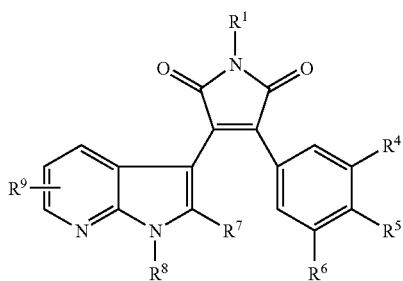

(Ib)

wherein $R^1$ is as defined in claim 1, $R^4$, $R^5$ and $R^6$ are $C_1$-$C_6$-alkyl and $R^7$, $R^8$ and $R^9$ are as defined in any one of claim 1, 3 or 4.

9. The compounds of claim 1 having formula Ic

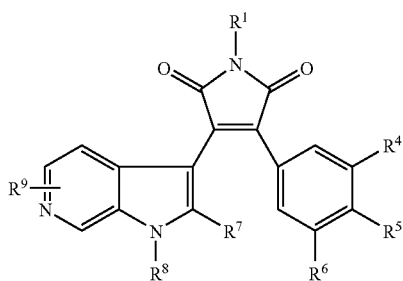

(Ic)

wherein $R^1$ is as defined in claim 1, $R^4$, $R^5$ and $R^6$ are $C_1$-$C_6$-alkyl and $R^7$, $R^8$ and $R^9$ are as defined in any one of claim 1, 3 or 4.

10. The compounds of claim 1 having formula Id

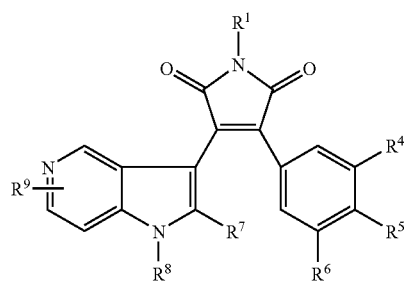

(Id)

wherein $R^1$ is as defined in claim 1, $R^4$, $R^5$ and $R^6$ are $C_1$-$C_6$-alkoxy and $R^7$, $R^8$ and $R^9$ are as defined in any one of claim 1, 3 or 4.

11. The compounds of claim 1 having formula Ie

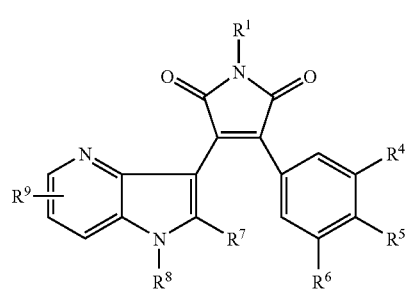

(Ie)

wherein $R^1$ is as defined in claim 1, $R^4$, $R^5$ and $R^6$ are as $C_1$-$C_6$-alkoxy and $R^7$, $R^8$ and $R^9$ are as defined in any one of claim 1, 3 or 4.

12. A pharmaceutical composition comprising at least one compound of formula I according to claim 1 and a pharmaceutically acceptable excipient.

* * * * *